United States Patent
Kuzma et al.

(10) Patent No.: US 8,538,554 B2
(45) Date of Patent: Sep. 17, 2013

(54) IMPLANTABLE ELECTRODE, INSERTION TOOL FOR USE THEREWITH, AND INSERTION METHOD

(75) Inventors: Janusz A. Kuzma, Parker, CO (US); Lani A. Smith, Parker, CO (US); Chuladatta Thenuwara, Castaic, CA (US); Tom Xiaohai He, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 691 days.

(21) Appl. No.: 12/212,427

(22) Filed: Sep. 17, 2008

(65) Prior Publication Data

US 2009/0024196 A1  Jan. 22, 2009

Related U.S. Application Data

(62) Division of application No. 11/124,843, filed on May 9, 2005, now Pat. No. 7,460,913.

(60) Provisional application No. 60/569,872, filed on May 10, 2004.

(51) Int. Cl.
*A61N 1/05* (2006.01)

(52) U.S. Cl.
USPC ........................................ 607/126; 607/128

(58) Field of Classification Search
USPC .................................. 607/126, 128
See application file for complete search history.

(56) References Cited

U.S. PATENT DOCUMENTS

| | | | |
|---|---|---|---|
| 3,769,984 A * | 11/1973 | Muench | 607/122 |
| 4,409,994 A * | 10/1983 | Doring | 607/126 |
| 4,506,679 A | 3/1985 | Mann | |
| 4,716,888 A * | 1/1988 | Wesner | 607/126 |
| 5,193,539 A | 3/1993 | Schulman | |
| 5,193,540 A | 3/1993 | Schulman | |
| 5,257,634 A | 11/1993 | Kroll | |
| 5,312,439 A | 5/1994 | Loeb | |
| 5,324,327 A * | 6/1994 | Cohen | 607/122 |
| 5,405,367 A | 4/1995 | Schulman et al. | |
| 6,051,017 A | 4/2000 | Loeb et al. | |
| 6,061,596 A | 5/2000 | Richmond et al. | |
| 6,151,526 A | 11/2000 | Tziviskos | |
| 6,175,764 B1 | 1/2001 | Loeb et al. | |
| 6,181,965 B1 | 1/2001 | Loeb et al. | |
| 6,185,452 B1 | 2/2001 | Schulman et al. | |
| 6,185,455 B1 | 2/2001 | Loeb et al. | |
| 6,214,032 B1 | 4/2001 | Loeb et al. | |
| 6,278,897 B1 * | 8/2001 | Rutten et al. | 607/122 |
| 6,315,721 B2 | 11/2001 | Schulman et al. | |
| 6,582,441 B1 | 6/2003 | He et al. | |
| 2003/0045919 A1 | 3/2003 | Swoyer et al. | |
| 2003/0114905 A1 | 6/2003 | Kuzma | |
| 2003/0199938 A1 * | 10/2003 | Smits et al. | 607/27 |
| 2004/0230280 A1 * | 11/2004 | Cates et al. | 607/126 |

\* cited by examiner

*Primary Examiner* — Kennedy Schaetzle
*Assistant Examiner* — Erica Lee
(74) *Attorney, Agent, or Firm* — Frommer Lawrence & Haug LLP; Bruce E. Black

(57) ABSTRACT

An electrode system includes an implantable electrode having at least one electrode contact, an insertion tool, and a technique or method that allows the electrode contact to be positioned within soft tissue at a selected target stimulation site.

18 Claims, 9 Drawing Sheets

IMPLANTABLE ELECTRODE, INSERTION TOOL FOR USE THEREWITH, AND INSERTION METHOD

RELATED APPLICATIONS

This application is a divisional of U.S. patent application Ser. No. 11/124,843, filed May 9, 2005, now U.S. Pat. 7,460,913, which claims benefit of U.S. Provisional Patent Application Ser. No. 60/569,872, filed May 10, 2004, both of which are incorporated herein by reference in their entirety.

FIELD

The present invention relates to electrodes, and more particularly to an implantable electrode that can be implanted within soft tissue for the stimulation of nerves or muscles, and an insertion tool and method of insertion for use therewith. Such electrode may be used with an implantable microstimulator, or with other types of stimulators.

BACKGROUND

Microstimulators are known in the art. For example, in U.S. Pat. No. 5,312,439, incorporated herein by reference, entitled "Implantable Device Having an Electrolytic Storage Electrode," an implantable micro-stimulation device for tissue stimulation is described. The described microstimulator shown in the '439 patent relates to an implantable device using one or more exposed, electrolytic electrodes to store electrical energy received by the implanted device, for the purpose of providing electrical energy to at least a portion of the internal electrical circuitry of the implantable device. It uses an electrolytic capacitor electrode to store electrical energy in the electrode when exposed to body fluids.

Another microstimulator known in the art is described in U.S. Pat. No. 5,193,539, "Implantable Microstimulator", which patent is also incorporated herein by reference. The '539 patent describes a microstimulator in which power and information for operating the microstimulator is received through a modulated, alternating magnetic field in which a coil is adapted to function as the secondary winding of a transformer. The induction coil receives energy from outside the body and a capacitor is used to store electrical energy which is released to the microstimulator's exposed electrodes under the control of electronic control circuitry.

In U.S. Pat. No. 5,193,540, which patent is likewise incorporated herein by reference, a structure and method of manufacture of an implantable microstimulator is disclosed. The microstimulator has a structure which is manufactured to be substantially encapsulated within a hermetically-sealed housing inert to body fluids, and of a size and shape capable of implantation in a living body, with appropriate surgical tools. Within the microstimulator, an induction coil receives energy from outside the body requiring an external power supply. Another method of manufacturing a microstimulator is found in U.S. Pat. No. 5,405,367, which patent is also incorporated herein by reference and which patent is a continuation of the '540 patent.

In yet another example, U.S. Pat. No. 6,185,452, which patent is also incorporated herein by reference, describes a device configured for implanting beneath a patient's skin for the purpose of nerve or muscle stimulation and/or parameter monitoring and/or data communication. Such a device contains a power source for powering the internal electronic circuitry. Such power supply is a battery that may be externally charged each day. Similar battery specifications are found in U.S. Pat. No. 6,315,721, which patent is incorporated herein by reference.

Other microstimulator systems prevent and/or treat various disorders associated with prolonged inactivity, confinement or immobilization of one or more muscles. Such microstimulators are taught, e.g., in U.S. Pat. Nos. 6,061,596 (Method for Conditioning Pelvis Musculature Using an Implanted Microstimulator); 6,051,017 (Implantable Microstimulator and Systems Employing the Same); 6,175,764 (Implantable Microstimulator System for Producing Repeatable Patterns of Electrical Stimulation; 6,181,965 (Implantable Microstimulator System for Prevention of Disorders); 6,185,455 (Methods of Reducing the Incidence of Medical Complications Using Implantable Microstimulators); and 6,214,032 (System for Implanting a Microstimulator). The applications described in these additional patents, including the power charging techniques, may also be used with the present invention. The '596, '017, '764, '965, '455, and '032 patents are incorporated herein by reference.

Despite the various types of microstimulators known in the art, as illustrated by the examples cited above, significant improvements are still possible and desirable, particularly relative to positioning the microstimulator at a desired target site within the tissue to be stimulated.

Thus, it is seen that there is a need in the art for a simple electrode system that can be easily placed within soft tissue for the stimulation of nerves or muscles.

SUMMARY

The present invention addresses the above and other needs by providing an electrode system, including an implantable electrode having one or more electrode contacts, an insertion tool, and a technique (method of implanting) that can be used with the electrode and insertion tool to precisely position the electrode contacts) within soft tissue at a selected target stimulation site(s).

The present invention has primary applicability for use with a BION® micro-stimulator of the type made by Advanced Bionics Corporation of Valencia, Calif., as described above in many of the referenced U.S. patents. However, it is to be understood that the invention—an electrode, and an insertion tool for use with the electrode, and an insertion method—need not be limited to use with a BION-type microstimulator. Any other type of stimulator may be connected to the electrode of the present invention.

In at least some embodiments, an electrode, and/or an array of electrodes, is provided wherein the stimulating contact(s) associated with the electrode can be readily placed within soft tissue precisely at a desired target stimulation site(s).

In at least some embodiments, a technique or method for implanting such an electrode is provided wherein the electrode contacts are maintained in a stable position at the target stimulation site both during the insertion process and after the insertion process.

In at least some embodiments, an insertion technique or method is provided that is easy to perform and provides minimum trauma to the patient within whom the electrode is implanted.

In at least some embodiments, an electrode and insertion tool and technique for use with such electrode is provided having all the features as described above, and in addition allows the electrode to be repositioned, if necessary. To this end, in at least some embodiments ease of explanation and re-implantation is provided.

In at least some embodiments, a low cost technique is provided that includes the benefit of effective patient screening prior to making the decision to implant the stimulator, e.g., the BION® microstimulator (or other stimulator). That is, the present invention allows the electrode contact(s) to be precisely positioned within the target tissue and such electrode contact(s) has(have) a lead wire attached thereto. Such lead wire can be easily connected to a suitable trial (external) stimulator in order to allow the patient to experience stimulation at the target site, thereby confirming over a suitable trial period whether such stimulation is effective or not prior to actually implanting a neural stimulator that will provide electrical stimulation at the target site.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
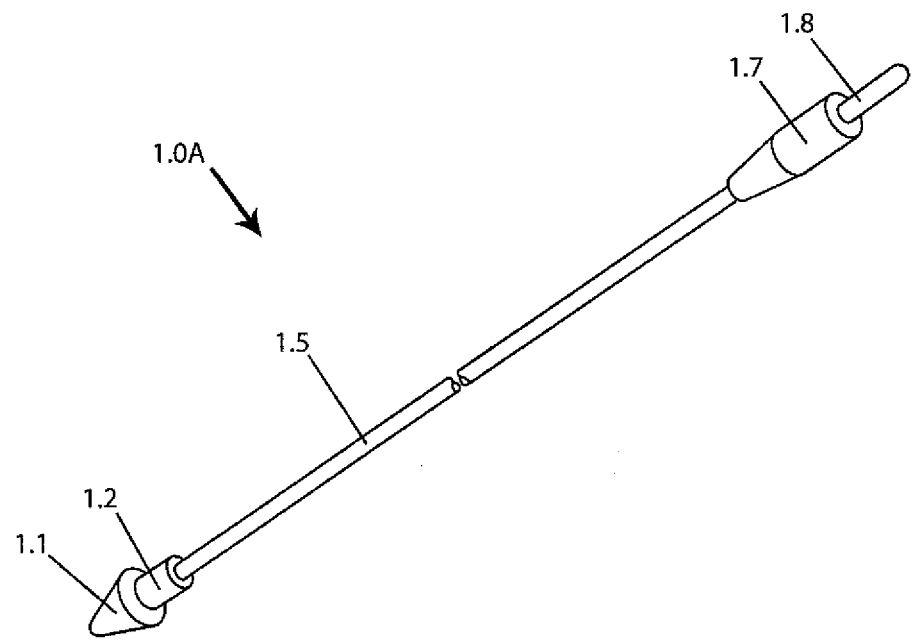
FIG. 1A illustrates the construction of one embodiment of the electrode system of the present invention.
Figure 1B:
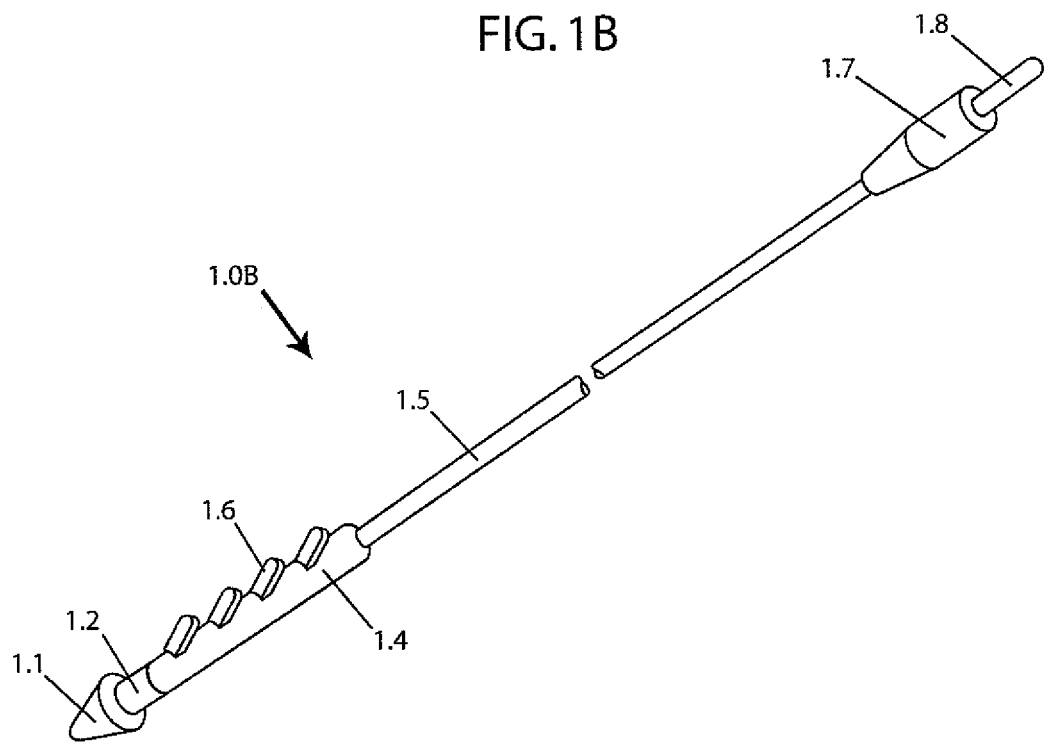
FIG. 1B illustrates the construction of another embodiment of the electrode system of the present invention, such embodiment including barbs near the distal tip.

Turning first to FIGS. 1A and 1B, the construction of a no-barbs embodiment (FIG. 1A) and a one-row-of-barbs embodiment (FIG. 1B) of the invention is illustrated. At a distal tip of both embodiments is a stimulating contact 1.1. This contact is preferably made from platinum or a platinum alloy. The contact 1.1 has a welded tubular neck 1.2 preferably made from the same material, i.e., platinum of a platinum alloy. An insulated multi-filament conductor 1.5, sometimes referred to as the "wire", is welded on one side to the contact 1.1. Near the proximal end of the electrode, such multi-filament conductor is welded to a connector plug 1.8. Connector plug 1.8 is over-molded with a silicone body 1.7.

In the embodiment shown in FIG. 1B, the lead wire 1.5 is further over-molded with anchoring tube 1.4. The anchoring tube 1.4 has a number of barbs 1.6 formed thereon. For the embodiment shown in FIG. 1B, the barbs are formed in a single row.

Figure 2A:
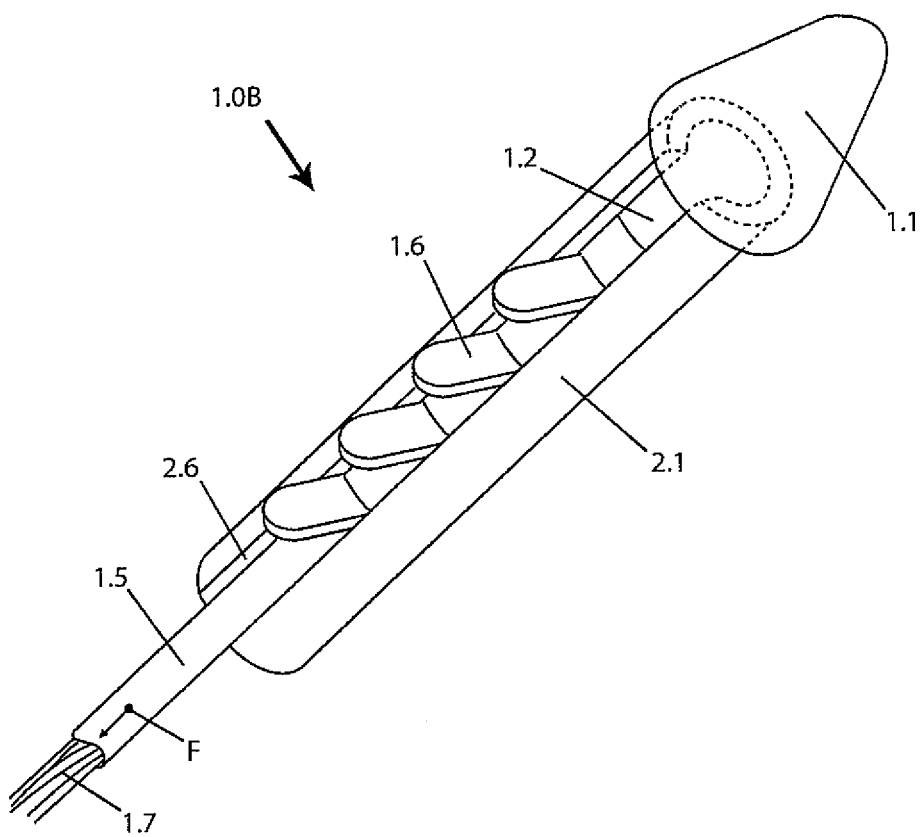
FIG. 2A illustrates in more detail the construction of the electrode tip section of FIG. 1B and its position within a slotted insertion tube.
Figure 2B:
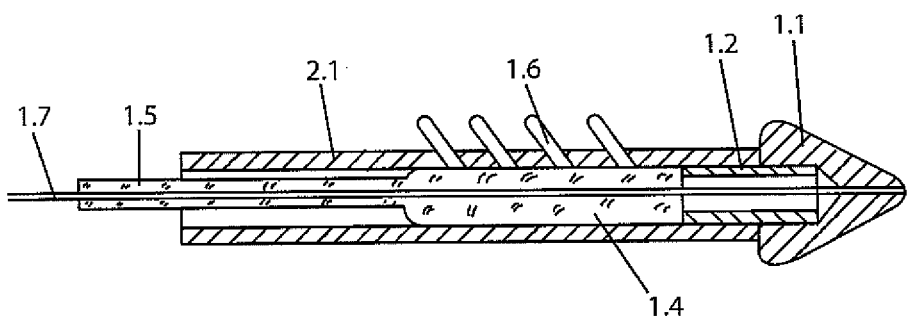
FIG. 2B shows a cross-sectional view of the electrode tip section of FIG. 2A.

FIG. 2A and FIG. 2B illustrate in more detail the construction of the electrode tip section and its position within a slotted insertion tube 2.1. Note that FIG. 2B is a sectional view of the electrode tip and tube shown in FIG. 2A.

As seen in FIGS. 2A and 2B, an important element of this embodiment of the invention is the positioning of barbs 1.6 in a row so as to slidably fit within slot 2.6 of insertion tube 2.1. The round body of anchoring tube 1.4 and its barbs 1.6 are able to move freely within the insertion tube. Further, the electrode lead has a thinner section, e.g., it's body portion 1.5 (the insulated multi-filar conductor) which can be easily pulled out through the slot 2.6 of the insertion tube.

The electrode lead, when loaded into the insertion tool, is under tension F (FIG. 2A). This tension force F maintains a stable position of the electrode tip 1.1. This stable position is achieved by a combination of tension force F and the interlocking of the neck 1.2 within internal diameter of insertion tube 2.1. The slot 2.3 of the insertion tube 2.1 is smaller than neck 1.2 and round body 1.4.

Figure 3:
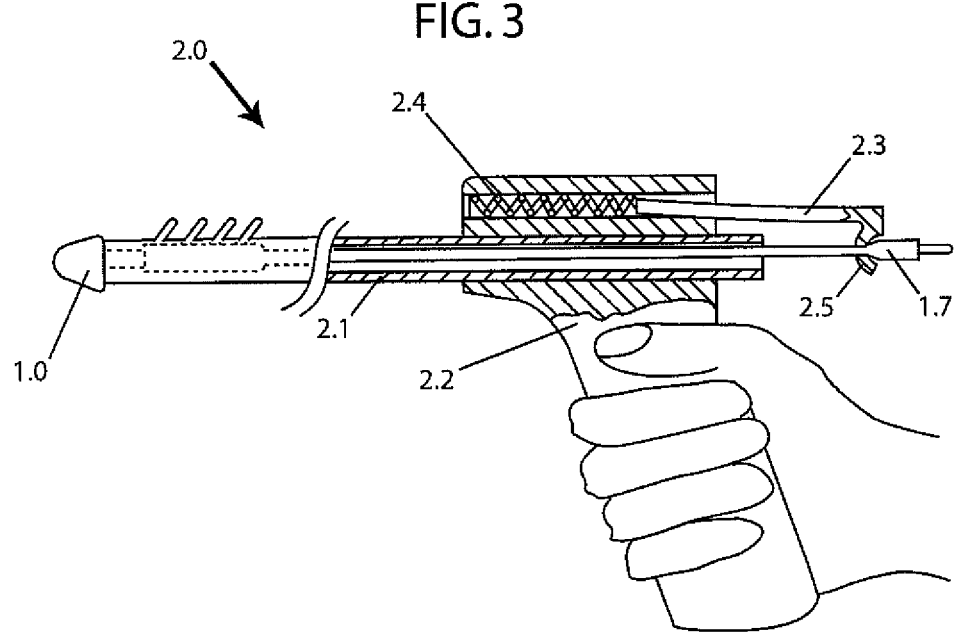
FIG. 3 shows the construction and operation of an insertion tool used with the invention.

FIG. 3 illustrates the construction and operation of the insertion tool 2.0. As seen in FIG. 3, the main functional part of the insertion tool is slotted insertion tube 2.1, which may have an increased diameter towards the handle 2.2 to increase necessary stiffness. The tube 2.1 is assembled within the handle 2.2. The slot 2.3 of the tube 2.1 is aligned with a slot (not shown in FIG. 3) in the handle 2.2. The slot in the tube 2.1 and handle 2.2 is large enough to allow free passage of the electrode body lead 1.5.

Still with reference to FIG. 3, the handle 2.2 contains slider 2.3 equipped with a hook 2.5. The slider is pushed back by internal spring 2.4. After placing the electrode contact 1.1 inside the distal opening of the insertion tube, the lead connector 1.7 is hooked to the slider 2.3 using hook 2.5, thereby providing the desired stabilizing force F.

Figure 4:
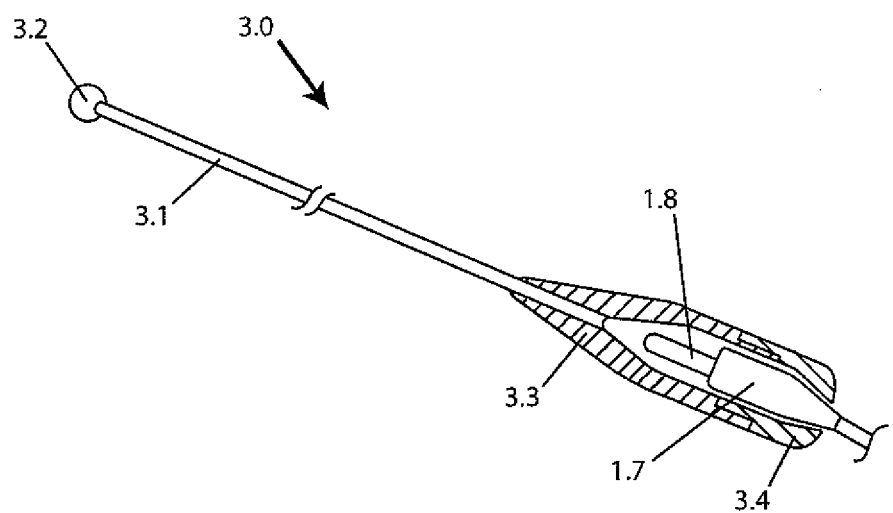
FIG. 4 depicts the construction of a tunneling tool that may be used with the invention.

Turning next to FIG. 4, a tunneling tool 3.0 is shown attached to the over-molded silicon body 1.7 of the connector plug 1.8. The main part of the tunneling tool 3.0 is a bendable wire 3.1 equipped on one end with a guiding ball 3.2. The ball 3.2 reduces the danger of perforating the skin or organs during tunneling.

At the opposite end of the tunneling tool 3.0 (which opposite end is adapted to connect to the connector plug 1.8) is a two-part container 3.3 and 3.4. Container 3.4 is adapted to engage with container 3.3, e.g., by way of a threaded engagement, or a clip-lock engagement. Part 3.4 holds silicone body 1.7 and the two parts 3.3 and 3.4 engage together to protect the connector plug during tunneling.

Figure 5A:
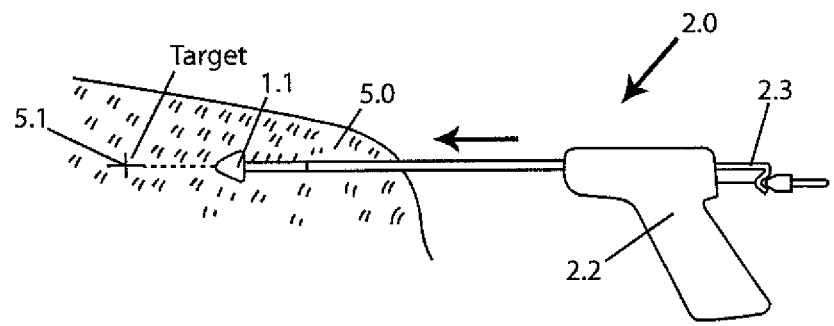
FIGS. 5A, 5B and 5C illustrate the method of the invention, with FIG. 5A showing the insertion process, FIG. 5B showing the release of the lead connector, and FIG. 5C showing the removal of the insertion tool.
Figure 5B:
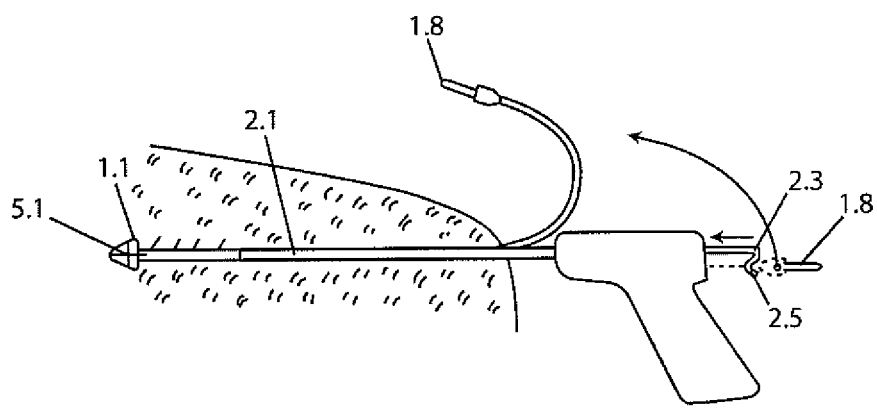
Figure 5C:
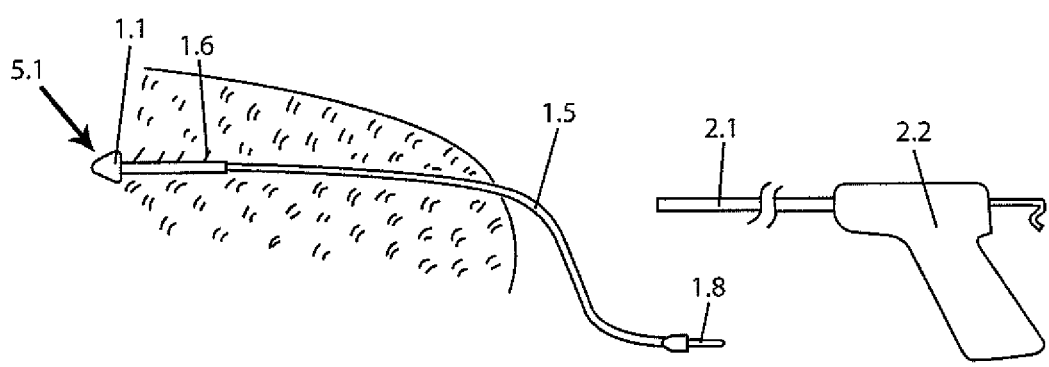

FIGS. 5A, 5B and 5C illustrate the insertion process. In FIG. 5A, the insertion tool 2.0, is used to place the stimulating contact 1.1 at the target tissue location 5.1 within soft body tissue 5.0. That is, with the electrode 1.0A or 1.0B inserted in the insertion tube 2.1, and with the insertion tube held by handle 2.2, and with the electrode being held under a tension force F while in the insertion tube 2.1, the electrode contact

1.1, which has a sharp distal point like an arrow or needle, is pushed through the tissue until the stimulating contact 1.1 reaches the target site 5.1.

Once the stimulating contact is at the target tissue location 5.1, the connector plug 1.8 is released from the hook 2.5 by pushing the slider 2.3 towards the handle 2.2 of the insertion tool 2.0, as shown in FIG. 5B. The electrode lead body 1.5 is then allowed to slip out of the insertion tube 2.1 through the longitudinal slot 2.3 of the insertion tube. The insertion tube is then withdrawn, as shown in FIG. 5C, leaving the stimulating contact 1.1 and lead body 1.5 intact within the tissue. The barbs 1.6, help hold the electrode in place as the insertion tube is withdrawn.

With the stimulating contact 1.1 at the target location 5.1, the connector plug 1.8 may then be connected to a suitable neurostimulator in order to provide electrical stimulation pulses to the target site 5.1, and the efficacy of stimulating tissue at the target site 5.1 can be determined.

Figure 6A:
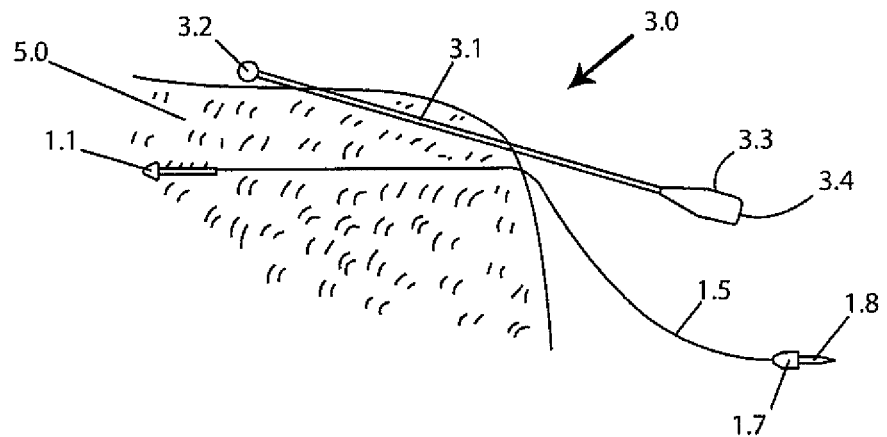
FIGS. 6A, 6B and 6C illustrate the process of tunneling.
Figure 6B:
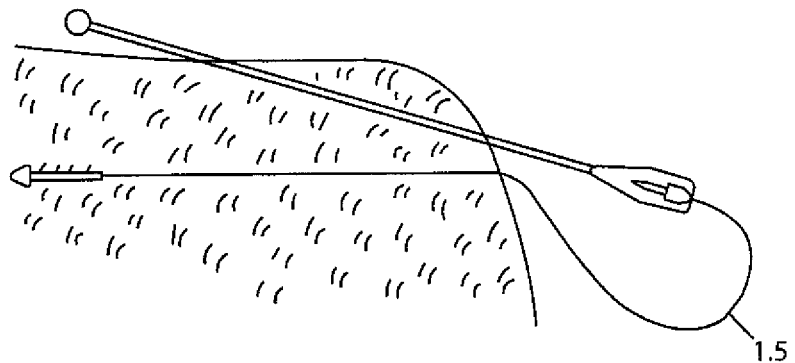
Figure 6C:
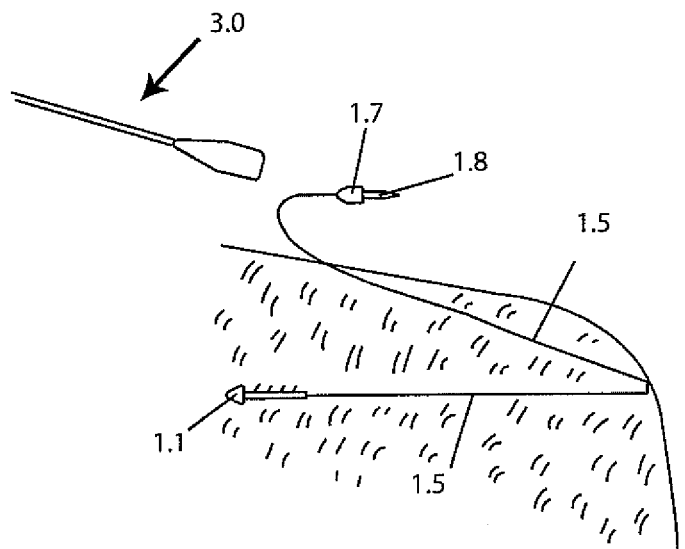

Should tunneling be required, e.g., to connect the connector plug to a neurostimulator at a different location, the process shown in FIGS. 6A, 6B and 6C may be used. Such process involves using the tunneling tool 3.0 to force the wire 3.1 of the tunneling tool through the soft tissue 5.0 to a desired location (FIG. 6A). The connector plug 1.8 is then placed in the two part container 3.3/3.4 of the tunneling tool (FIG. 6B). The tunneling tool is then pulled through the tissue, carrying the connector plug 1.8 through the tissue, to a new location (FIG. 6C), where it may be connected to a neurostimulator, e.g., the BION® microstimulator, or a suitable trial stimulator.

Figure 7A:
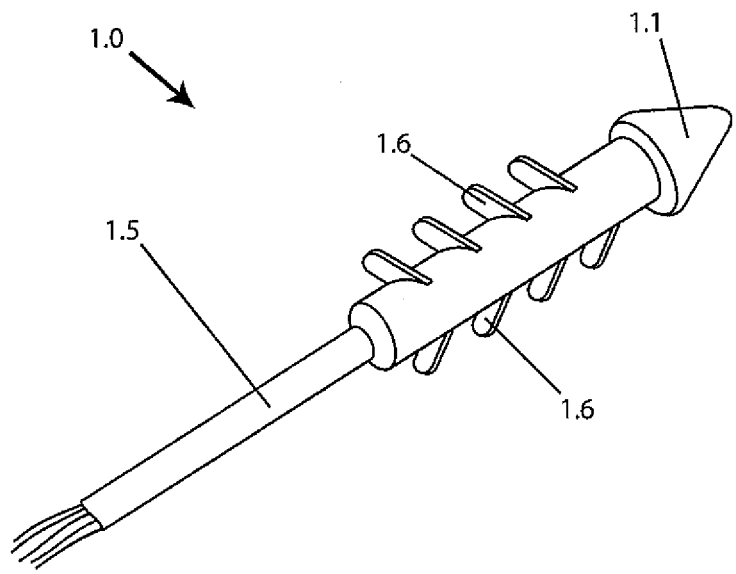
FIGS. 7A and 7B illustrate an alternative embodiment wherein two or more rows of barbs are employed.
Figure 7B:
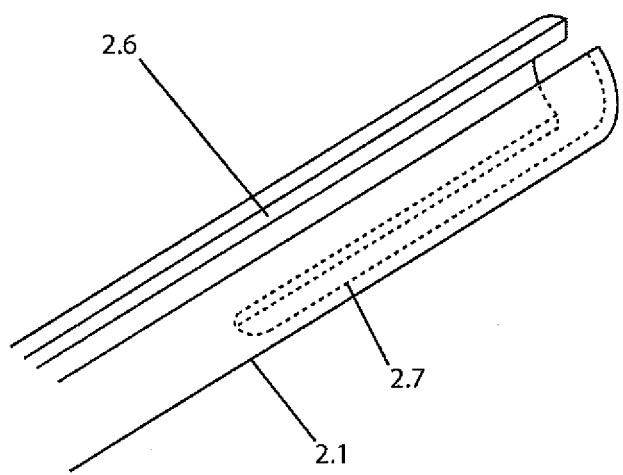

FIGS. 7A and 7B illustrate how the insertion tube 2.1 is modified when an electrode embodiment is employed having two rows of barbs 1.6. As seen best in FIG. 7B, the insertion tube 2.1 has an additional partial slot 2.7 formed therein, in addition to is main longitudinal slot 2.6. As the electrode 1.0 is placed within the insertion tube 2.1, the second row of barbs 1.6 fits within the second slot 2.7, whereas the first row of barbs fits within the primary slot 2.6.

Figure 8A:
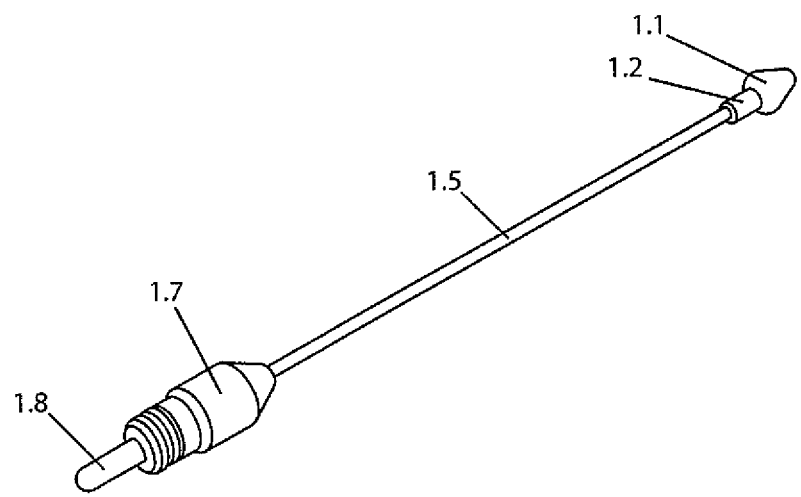
FIGS. 8A, 8B and 8C respectively illustrate the no barbs, one row of barbs, and two rows of barbs embodiments of the invention.
Figure 8B:
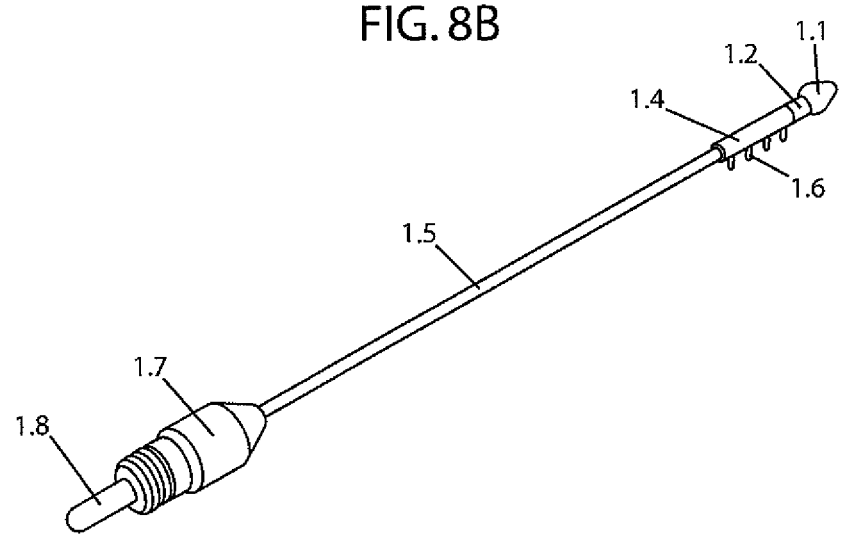
Figure 8C:
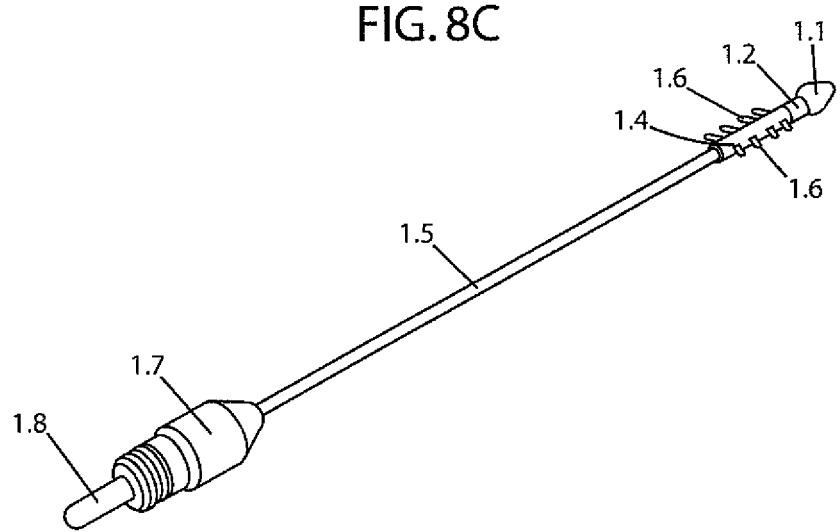

FIGS. 8A, 8B and 8C are depictions of the no-barb embodiment of the electrode (FIG. 8A), the one-row-of-barbs embodiment (FIG. 8B), and the two row-of-barbs embodiment (FIG. 8C). The reference numerals of these figures refer to elements previously described.

Figure 9:
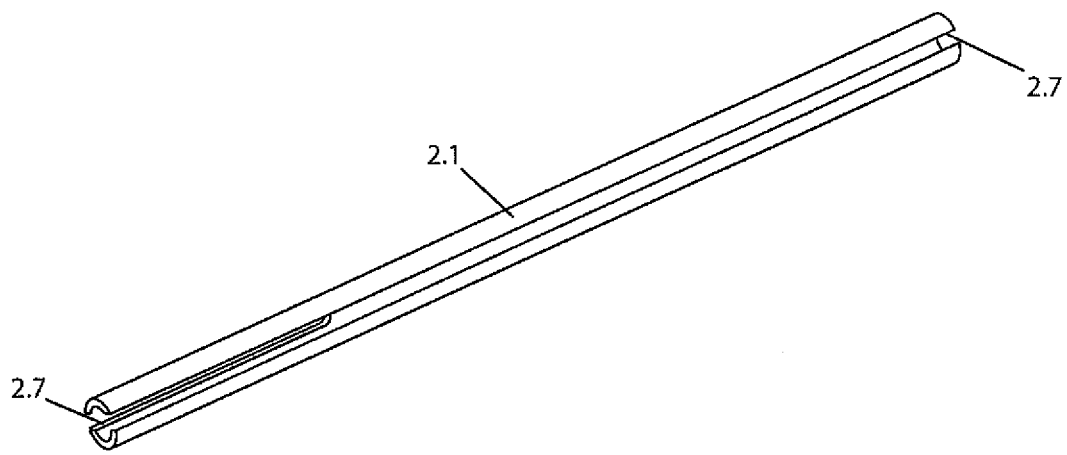
FIG. 9 illustrates an insertion tube that may be used when inserting the electrode of the invention.

FIG. 9 is a depiction of the insertion tube 2.1, having a first longitudinal slot 2.6 along its entire length, and a short slot 2.7 opposite the slot 2.6. For clarity, the insertion tool handle 2.0, slider 2.3 and other elements of the insertion tool 2.0 shown in FIG. 3, are not shown in FIG. 9.

Figure 10:
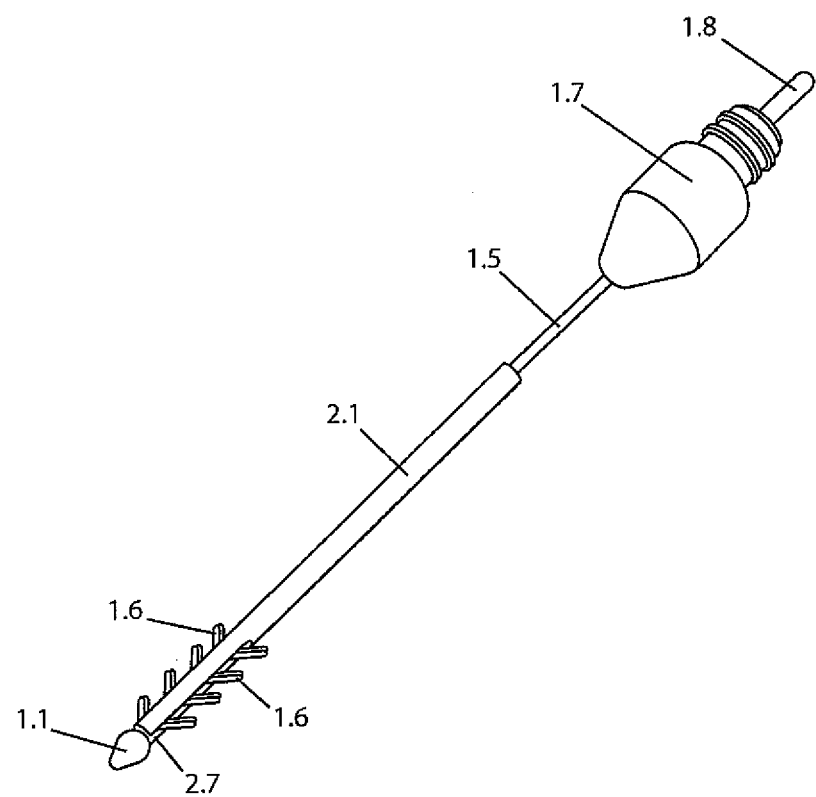
FIG. 10 shows the two-rows-of-barbs embodiment electrode of FIG. 8C inserted into the insertion tube of FIG. 9.

FIG. 10 depicts an embodiment of the electrode having two rows of barbs inserted into the insertion tube 2.1 of FIG. 9. Again, for clarity, many elements of the insertion tool 2.0 shown in FIG. 3 are omitted from FIG. 10. The insertion tube will require additional partial slot(s) to accommodate additional rows of barbs.

Figure 11:
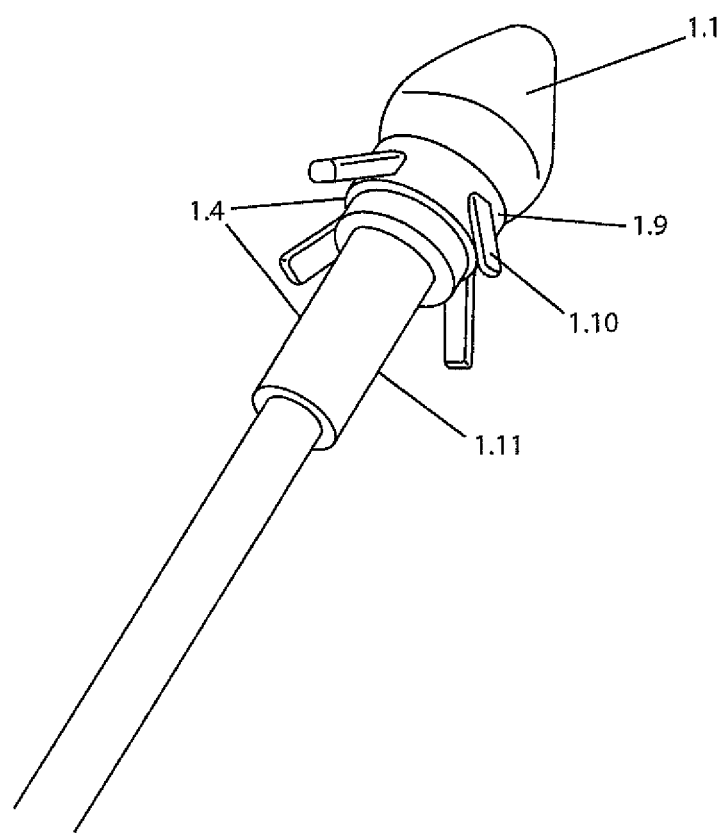
FIG. 11 illustrates the construction of another embodiment of the electrode system of the present invention.

FIG. 11 depicts another embodiment of the electrode with a collar 1.9 and barbs 1.10 disposed on the collar. The collar 1.9 is disposed below the contact 1.1 and is part of the anchoring tube 1.4. The collar can have an outer diameter that is greater than the inner diameter of the insertion tube 2.1 so that the insertion tube does not go over the collar 1.9 during the insertion process. The anchoring tube 1.4 may include a second portion 1.11 over which the insertion tube can fit. Accordingly, in such an embodiment no accommodation needs to be made in the insertion tube 2.1 for barbs 1.10 that are disposed on the collar 1.9. For example, an insertion tube can include only a single slot sized for removal of the electrode body lead 1.5 through the slot.

The second portion 1.11 of the anchoring tube 1.4 can be made of an insulative material, e.g., implantable polymers or Teflon. Use of the insulative second portion 1.11 allows electrical testing of electrode effectiveness to stimulate tissue during placement.

The barbs can be arrayed in any arrangement around the collar 2.1. For example, the barbs can be disposed along one or more concentric circles around the collar 1.9. It will be recognized that barbs can also be placed both on the collar 1.9 and on the second portion 1.11 of the anchoring tube 1.4, if desired. In some embodiments, the collar 1.9 and barbs 1.10 are formed of plastic (e.g., silicone) or ceramic and can be molded around the neck 1.2 (see FIG. 2A), if desired.

In one embodiment, a very flexible arrangement can be formed using flexible conductive fibers. The multi-filament conductor 1.6 can include many strands of very thin conductive fibers. For example, the fibers can have diameters in the range of 1 to 500 μm, preferably in the range of 10 to 25 μm. Any number of fibers can be used to form the bundle including several hundred (e.g., at least 100 and up to 500 or more) fibers. One example of suitable fibers are thin stainless steel fibers which can be bundled together to form the conductor 1.6. At one end the fibers are connected (e.g., welded) to the contact 1.1. At the other end, the fibers are connected to the connector plug 1.8. In one example of a method of making such a connection, the fibers can be passed through a metal tube (e.g., a platinum tube) and, optionally, the tube can be smashed against the fibers. The fibers are welded to the tube. This tube can then be then coupled to the connector plug (e.g., by welding).

The following features of the invention are believed to be unique: (1) a contact construction wherein the neck 1.2 fits snugly within the insertion tube 2.1; (2) electrode stabilization achieved by having the neck 1.2 and lead 1.5 under tension during the insertion process; (3) the removal of the lead 1.5 through the longitudinal slot 2.6 in the tube 2.1 and handle 2.2; (4) the use of barbs 1.6 aligned in a row on a least one side of the electrode lead near its distal end; (5) allowing the rows of barbs to readily slide through the slot(s) during deployment of the electrode; and (6) the possibility of tunneling the proximal end of the electrode to a different location using a special tunneling tool.

While the invention herein disclosed has been described by means of specific embodiments and applications thereof, numerous modifications and variations could be made thereto by those skilled in the art without departing from the scope of the invention set forth in the claims.

What is claimed is:

1. A system for implanting an implantable electrode lead comprising:
   an implantable electrode lead, comprising:
   a metal electrode contact at a distal end of the implantable electrode lead, wherein a distal end of the electrode contact has a conical shape with an arrow-like or needle-like distal point;
   a connector plug at a proximal end;
   an insulated conductor that electrically connects the connector plug to the metal electrode contact;
   a non-conductive anchoring tube proximate to the electrode contact with at least one row of flexible barbs protruding therefrom, the anchoring tube, excluding the barbs, having an outer diameter less than an outer diameter of a widest portion of the metal electrode contact; and
   a body portion extending at least from the anchoring tube to the connector plug, wherein the body portion proximal to the anchoring tube has an outer diameter less than the outer diameter of the anchoring tube; and an insertion tool, comprising an insertion tube defining an outer surface and an interior lumen, wherein the interior lumen is configured and arranged to removably receive at least the body portion, wherein the insertion tube further defines a longitudinal slot extending through the insertion tube from the outer surface of the insertion tube to the interior lumen, wherein the longitudinal slot extends an entire length of the insertion tube and has a width that is greater than the outer diameter of the body portion and less than the outer diameter of the non-conductive anchoring tube; and a handle comprising a slider and a hook attached to the slider, wherein the hook is configured and arranged to attach to the connector plug and provide a stabilizing force during implantation.

2. The implantable electrode lead of claim 1, wherein the at least one row of flexible barbs extends longitudinally along the non-conductive anchoring tube.

3. The implantable electrode lead of claim 2, wherein the at least one row of flexible barbs comprises two rows of flexible barbs extending longitudinally along the non-conductive anchoring tube.

4. The implantable electrode lead of claim 3, wherein the two rows of flexible barbs are located on opposite sides of the non-conductive anchoring tube.

5. The implantable electrode lead of claim 1, wherein the at least one row of flexible barbs is disposed in a concentric circle around, and protrudes from, the non-conductive anchoring tube.

6. The implantable electrode lead of claim 5, wherein the non-conductive anchoring tube comprises a collar proximate to the metal electrode contact and having an outer diameter greater than an outer diameter of another portion of the non-conductive anchoring tube, wherein at least a portion of the flexible barbs are disposed on the collar.

7. The implantable electrode lead of claim 1, wherein the non-conductive anchoring tube comprises a collar proximate to the metal electrode contact and a second portion proximal to the collar, wherein the at least one row of flexible barbs comprises at least one row of the flexible barbs disposed in a concentric circle around, and protruding from, the collar of the non-conductive anchoring tube and at least one row of the flexible barbs disposed on the second portion of the non-conductive anchoring tube.

8. The implantable electrode lead of claim 7, wherein the collar has an outer diameter greater than an outer diameter of the second portion of the non-conductive anchoring tube.

9. The implantable electrode lead of claim 1, wherein the insulated conductor comprises a plurality of thin fibers, each fiber having a diameter of between about 10 to 25 µm.

10. The implantable electrode lead of claim 1, wherein the flexible barbs are formed of plastic or ceramic.

11. The implantable electrode lead of claim 1, wherein the non-conductive anchoring tube is made of polymer.

12. A method for implanting an implantable electrode lead, wherein the method comprises:

providing the system of claim 1;

placing the implantable electrode lead under tension within the insertion tube, with the metal electrode contact at one end of the insertion tube, and with the connector plug at the other end of the insertion tube and attached to the hook of the handle;

directing the metal electrode contact, while held in the insertion tube under tension, through soft tissue to a desired tissue target location;

removing the tension from the implantable electrode lead held in the insertion tube by releasing the connector plug from the hook; and removing the insertion tube from the implantable electrode lead by passing the insulated conductor through the longitudinal slot, while leaving the metal electrode contact at the desired target location.

13. The method of claim 12, further comprising tunneling the insulated conductor through soft tissue using a tunneling tool.

14. The method of claim 12, further comprising coupling the connector plug, to a neurostimulator.

15. The method of claim 14, wherein the neurostimulator is a microstimulator.

16. The method of claim 12, wherein placing the implantable electrode lead under tension within the insertion tube comprises aligning at least one row of the flexible barbs with the longitudinal slot of the insertion tube so that the flexible barbs are positioned within the longitudinal slot.

17. The method of claim 12, wherein the insertion tube comprises a second longitudinal slot extending from a distal end of the insertion tube to a position between the distal and proximal ends of the insertion tube.

18. The method of claim 17, wherein the implantable electrode lead comprise a first row of flexible barbs and a second row of flexible barbs and wherein placing the implantable electrode lead under tension within the insertion tube comprises aligning the first row of flexible barbs with the longitudinal slot of the insertion tube so that the flexible barbs of the first row are positioned within the longitudinal slot and aligning the second row of flexible bars with the second longitudinal slot of the insertion tube so that the flexible barbs of the second row are positioned within the second longitudinal slot.

\* \* \* \* \*